US009716939B2

(12) United States Patent
Di Censo et al.

(10) Patent No.: US 9,716,939 B2
(45) Date of Patent: Jul. 25, 2017

(54) SYSTEM AND METHOD FOR USER CONTROLLABLE AUDITORY ENVIRONMENT CUSTOMIZATION

(71) Applicant: Harman International Industries, Inc., Stamford, CT (US)

(72) Inventors: Davide Di Censo, San Mateo, CA (US); Stefan Marti, Oakland, CA (US); Ajay Juneja, Mountain View, CA (US)

(73) Assignee: HARMAN INTERNATIONAL INDUSTRIES, INC., Stamford, CT (US)

( * ) Notice: Subject to any disclaimer, the term of this patent is extended or adjusted under 35 U.S.C. 154(b) by 473 days.

(21) Appl. No.: 14/148,689

(22) Filed: Jan. 6, 2014

(65) Prior Publication Data

US 2015/0195641 A1 Jul. 9, 2015

(51) Int. Cl.

*A61F 11/06* (2006.01)
*G10K 11/16* (2006.01)
*H03B 29/00* (2006.01)
*H04R 1/10* (2006.01)
*H04R 25/00* (2006.01)

(52) U.S. Cl.

CPC ........... *H04R 1/1083* (2013.01); *H04R 25/50* (2013.01); *H04R 2225/41* (2013.01); *H04R 2430/00* (2013.01); *H04R 2460/01* (2013.01)

(58) Field of Classification Search

CPC .............. H04R 1/1083; H04R 2225/41; H04R 2430/00; H04R 2460/01; H04R 25/50
USPC ..... 381/17, 56, 57, 71.6, 92, 94.1, 122, 317, 381/318, 328, 329; 340/3.5, 5.1, 11.1, 340/309.6, 438; 700/94
See application file for complete search history.

(56) References Cited

U.S. PATENT DOCUMENTS 5,027,410 A 6/1991 Williamson et al.
6,989,744 B2 1/2006 Proebsting
7,512,247 B1 3/2009 Odinak et al.
(Continued)

FOREIGN PATENT DOCUMENTS

WO 2008103925 A1 8/2008

OTHER PUBLICATIONS

Basu et al., "Smart Headphones", Proceedings of CHI 2001, Seattle, WA, pp. 267-268, http://alumni.media.mit.edu/~sbasu/papers/chi2001.pdf.
(Continued)

*Primary Examiner* — Paul S Kim
(74) *Attorney, Agent, or Firm* — Artegis Law Group, LLP

(57) ABSTRACT

A method for generating an auditory environment for a user may include receiving a signal representing an ambient auditory environment of the user, processing the signal using a microprocessor to identify at least one of a plurality of types of sounds in the ambient auditory environment, receiving user preferences corresponding to each of the plurality of types of sounds, modifying the signal for each type of sound in the ambient auditory environment based on the corresponding user preference, and outputting the modified signal to at least one speaker to generate the auditory environment for the user. A system may include a wearable device having speakers, microphones, and various other sensors to detect a noise context. A microprocessor processes ambient sounds and generates modified audio signals using attenuation, amplification, cancellation, and/or equalization based on user preferences associated with particular types of sounds.

26 Claims, 5 Drawing Sheets

(56) References Cited

U.S. PATENT DOCUMENTS

| | | | |
|---|---|---|---|
| 8,081,780 | B2 | 12/2011 | Goldstein et al. |
| 2005/0036637 | A1 | 2/2005 | Janssen |
| 2005/0226425 | A1 | 10/2005 | Polk, Jr. |
| 2008/0267416 | A1 | 10/2008 | Goldstein et al. |
| 2010/0076793 | A1 | 3/2010 | Goldstein et al. |
| 2011/0069843 | A1 | 3/2011 | Cohen et al. |
| 2011/0107216 | A1 | 5/2011 | Bi |
| 2012/0215519 | A1 | 8/2012 | Park et al. |
| 2013/0273967 | A1 | 10/2013 | Dave et al. |
| 2015/0071457 | A1 | 3/2015 | Burch |

OTHER PUBLICATIONS

Extended European Search Report for EP 14 19 9731 dated May 27, 2015.
Final Office Action dated Jan. 11, 2016, for U.S. Appl. No. 14/147,445.
Mueller et al., "Transparent Hearing", (CHI 2002), http://floydmueller.com/projects/transparent_hearing/ 1 page.
Non-Final Office Action dated Sep. 15, 2015, for U.S. Appl. No. 14/147,445.
International Search Report and Written Opinion for PCT/US2015/010234 dated Apr. 29, 2015.

SYSTEM AND METHOD FOR USER CONTROLLABLE AUDITORY ENVIRONMENT CUSTOMIZATION

TECHNICAL FIELD

This disclosure relates to systems and methods for a user controllable auditory environment using wearable devices, such as headphones, speakers, or in-ear devices, for example, to selectively cancel, add, enhance, and/or attenuate auditory events for the user.

BACKGROUND

Various products have been designed with the goal of eliminating unwanted sounds or "auditory pollution" so that users can listen to a desired audio source or substantially eliminate noises from surrounding activities. More and more objects, events, and situations continue to generate auditory information of various kinds. Some of this auditory information is welcomed, but much of it may be perceived as distracting, unwanted, and irrelevant. One's natural ability to focus on certain sounds and ignore others is continually challenged and may decrease with age.

Various types of noise cancelling headphones and hearing aid devices allow users some control or influence over their auditory environment. Noise cancelling systems usually cancel or enhance the overall sound field, but do not distinguish between various types of sounds or sound events. In other words, the cancellation or enhancement is not selective and cannot be finely tuned by the user. While some hearing aid devices can be tuned for use in certain environments and settings, those systems often do not provide desired flexibility and fine grained dynamic control to influence the user's auditory environment. Similarly, in-ear monitoring devices, such as worn by artists on stage, may be fed with a very specific sound mix prepared by a monitor mixing engineer. However, this is a manual process, and uses only additive mixing.

SUMMARY

Embodiments according to the present disclosure include a system and method for generating an auditory environment for a user that may include receiving a signal representing an ambient auditory environment of the user, processing the signal using a microprocessor to identify at least one of a plurality of types of sounds in the ambient auditory environment, receiving user preferences corresponding to each of the plurality of types of sounds, modifying the signal for each type of sound in the ambient auditory environment based on the corresponding user preference, and outputting the modified signal to at least one speaker to generate the auditory environment for the user. In one embodiment, a system for generating an auditory environment for a user includes a speaker, a microphone, and a digital signal processor configured to receive an ambient audio signal from the microphone representing an ambient auditory environment of the user, process the ambient audio signal to identify at least one of a plurality of types of sounds in the ambient auditory environment, modify the at least one type of sound based on received user preferences; and output the modified sound to the speaker to generate the auditory environment for the user.

Various embodiments may include receiving a sound signal from an external device in communication with the microprocessor, and combining the sound signal from the external device with the modified types of sound. The sound signal from an external device may be wirelessly transmitted and received. The external device may communicate over a local or wide area network, such as the internet, and may include a database having stored sound signals of different types of sounds that may be used in identifying sound types or groups. Embodiments may include receiving user preferences wirelessly from a user interface generated by a second microprocessor, which may be embedded in a mobile device, such as a cell phone, for example. The user interface may dynamically generate user controls to provide a context-sensitive user interface in response to the ambient auditory environment of the user. As such, controls may only be presented where the ambient environment includes a corresponding type or group of sounds. Embodiments may include one or more context sensors to identify expected sounds and associated spatial orientation relative to the user within the audio environment. Context sensors may include a GPS sensor, accelerometer, or gyroscope, for example, in addition to one or more microphones.

Embodiments of the disclosure may also include generating a context-sensitive user interface by displaying a plurality of controls corresponding to selected sounds or default controls for anticipated sounds in the ambient auditory environment. Embodiments may include various types of user interfaces generated by the microprocessor or by a second microprocessor associated with a mobile device, such as a cell phone, laptop computer, or tablet computer, wrist watch, or other wearable accessory or clothing, for example. In one embodiment, the user interface captures user gestures to specify at least one user preference associated with one of the plurality of types of sounds. Other user interfaces may include graphical displays on touch-sensitive screens, such as slider bars, radio buttons or check boxes, etc. The user interface may be implemented using one or more context sensors to detect movements or gestures of the user. A voice-activated user interface may also be provided with voice-recognition to provide user preferences or other system commands to the microprocessor.

The received ambient audio signal may be processed by dividing the signal into a plurality of component signals each representing one of the plurality of types of sounds, modifying each of the component signals for each type of sound in the ambient auditory environment based on the corresponding user preference, generating a left signal and a right signal for each of the plurality of component signals based on a corresponding desired spatial position for the type of sound within the auditory environment of the user, combining the left signals into a combined left signal, and combining the right signals into a combined right signal. The combined left signal is provided to a first speaker and the combined right signal is provided to a second speaker. Modifying the signal may include adjusting signal amplitude and/or frequency spectrum associated with one or more component sound types by attenuating the component signal, amplifying the component signal, equalizing the component signal, cancelling the component signal, and/or replacing one type of sound with another type of sound in the component signal. Cancelling a sound type or group may be performed by generating an inverse signal having substantially equal amplitude and substantially opposite phase relative to the one type or group of sound.

Various embodiments of a system for generating an auditory environment for a user may include a speaker, a microphone, and a digital signal processor configured to receive an ambient audio signal from the microphone representing an ambient auditory environment of the user, process the ambient audio signal to identify at least one of a plurality of types of sounds in the ambient auditory environment, modify the at least one type of sound based on received user preferences; and output the modified sound to the speaker to generate the auditory environment for the user. The speaker and the microphone may be disposed within an ear bud configured for positioning within an ear of the user, or within ear cups configured for positioning over the ears of a user. The digital signal processor or other microprocessor may be configured to compare the ambient audio signal to a plurality of sound signals to identify the at least one type of sound in the ambient auditory environment.

Embodiments also include a computer program product for generating an auditory environment for a user that includes a computer readable storage medium having stored program code executable by a microprocessor to process an ambient audio signal to separate the ambient audio signal into component signals each corresponding to one of a plurality of groups of sounds, modify the component signals in response to corresponding user preferences received from a user interface, and combine the component signals after modification to generate an output signal for the user. The computer readable storage medium may also include code to receive user preferences from a user interface having a plurality of controls selected in response to the component signals identified in the ambient audio signal, and code to change at least one of an amplitude or a frequency spectrum of the component signals in response to the user preferences.

Various embodiments may have associated advantages. For example, embodiments of a wearable device or related method may improve hearing capabilities, attention, and/or concentration abilities of a user by selectively processing different types or groups of sounds based on different user preferences for various types of sounds. This may result in lower cognitive load for auditory tasks and provide stronger focus when listening to conversations, music, talks, or any kind of sounds. Systems and methods according to the present disclosure may allow the user to enjoy only the sounds that he/she desires to hear from the auditory environment, enhance his/her auditory experience with functionalities like beautification of sounds by replacing noise or unwanted sounds with nature sounds or music, for example, and real-time translations during conversations, stream audio and phone conversations directly to his/her ears and be freed from the need of holding a device next to his/her ear, and add any additional sounds (e.g. music or voice recordings) to his/her auditory field, for example.

Various embodiments may allow the user to receive audio signals from an external device over a local or wide area network. This facilitates context-aware advertisements that may be provided to a user, as well as context-aware adjustments to the user interface or user preferences. The user may be given complete control over their personal auditory environment, which may result in reduced information overload and reduced stress.

The above advantages and other advantages and features of the present disclosure will be readily apparent from the following detailed description of the preferred embodiments when taken in connection with the accompanying drawings.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the teachings of the disclosure. As those of ordinary skill in the art will understand, various features illustrated and described with reference to any one of the figures may be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations. Some of the description may specify a number of components that may be used or a spatial reference in a drawing such as above, below, inside, outside, etc. Any such spatial references, references to shapes, or references to the numbers of components that may be utilized are merely used for convenience and ease of illustration and description and should not be construed in any limiting manner.

Figure 1:
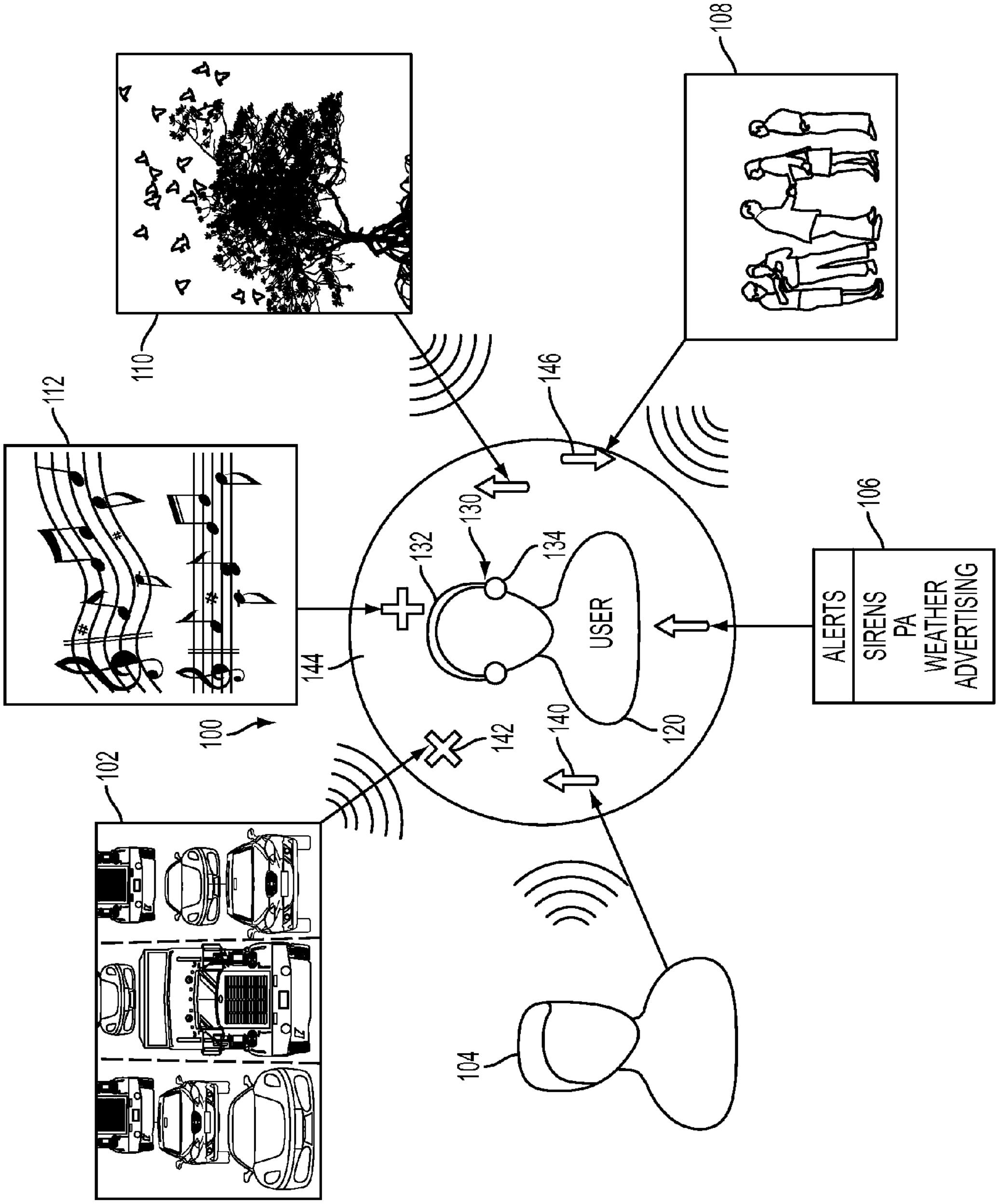
FIG. 1 illustrates operation of a representative embodiment of a system or method for generating a customized or personalized auditory environment for a user.

FIG. 1 illustrates operation of a representative embodiment of a system or method for generating a user controllable auditory environment for a user that may be personalized or customized in response to user preferences for particular types or groups of sounds. System 100 includes a user 120 surrounded by an ambient auditory environment including a plurality of types or groups of sounds. In the representative embodiment of FIG. 1, representative sound sources and associated types or groups of sounds are represented by traffic noise 102, a voice from a person 104 talking to user 120, various types of alerts 106, voices from a crowd or conversations 108 either not directed to user 120 or in a different spatial location than voice from person 104, nature sounds 110, and music 112. The representative types or groups of sound or noise (which may include any undesired sounds) illustrated in FIG. 1 are representative only and are provided as non-limiting examples. The auditory environment or ambient sounds relative to user 120 will vary as the user moves to different locations and may include tens or hundreds of other types of sounds or noises, some of which are described in greater detail with reference to particular embodiments below.

Various sounds, such as those represented in FIG. 1, may be stored in a database and accessed to be added or inserted into the auditory environment of the user in response to user preferences as described in greater detail below. Similarly, various signal characteristics of representative or average sounds of a particular sound group or sound type may be extracted and stored in a database. These signal characteristics of representative or average sounds of a particular sound group or sound type may be used as a signature to compare to sounds from a current ambient auditory environment to identify the type of sound or sound group within the ambient environment. One or more databases of sounds and/or sound signal characteristics may be stored on-board or locally within system 100 or may be accessed over a local or wide area network, such as the internet. Sound type signatures or profiles may be dynamically loaded or changed based on a current position, location, or context of user 120. Alternatively, one or more sound types or profiles may be downloaded or purchased by user 120 for use in replacing undesired sounds/noises, or for augmenting the auditory environment.

Similar to the stored sounds or representative signals described above, alerts 106 may originate within the ambient auditory environment of user 120 and be detected by an associated microphone, or may be directly transmitted to system 100 using a wireless communication protocol such as Wi-Fi, Bluetooth, or cellular protocols. For example, a regional weather alert or Amber alert may be transmitted and received by system 100 and inserted or added to the auditory environment of the user. Depending on the particular implementation, some alerts may be processed based on user preferences, while other alerts may not be subject to various types of user preferences, such as cancellation or attenuation, for example. Alerts may include context-sensitive advertisements, announcements, or information, such as when attending a concert, sporting event, or theater, for example.

As also shown in FIG. 1, system 100 includes a wearable device 130 that includes at least one microphone, at least one speaker, and a microprocessor-based digital signal processor (DSP) as illustrated and described in greater detail with reference to FIGS. 2-6. Wearable device 130 may be implemented by headphones or ear buds 134 that each contain an associated speaker and one or more microphones or transducers, which may include an ambient microphone to detect ambient sounds within the ambient auditory environment, and an internal microphone used in a closed loop feedback control system for cancellation of user selected sounds. Depending on the particular embodiment, the ear pieces 134 may be optionally connected by a headband 132, or may be configured for positioning around a respective ear of user 120. In one embodiment, earpieces 134 are in-the-ear devices that partially or substantially completely seal the ear canal of user 120 to provide passive attenuation of ambient sounds. In another embodiment, circumaural ear cups may be positioned over each ear to provide improved passive attenuation. Other embodiments may use supra-aural earpieces 134 that are positioned over the ear canal, but provide much less passive attenuation of ambient sounds.

In one embodiment, wearable device 130 includes in-the-ear or intra-aural earpieces 134 and operates in a default or initial processing mode such that earpieces 134 are acoustically "transparent", meaning the system 100 does not alter the auditory field or environment experienced by user 120 relative to the current ambient auditory environment. Alternatively, system 100 may include a default mode that attenuates all sounds or amplifies all sounds from the ambient environment, or attenuates or amplifies particular frequencies of ambient sounds similar to operation of more conventional noise cancelling headphones or hearing aids, respectively. In contrast to such conventional systems, user 120 may personalize or customize his/her auditory environment using system 100 by setting different user preferences applied to different types or groups of sounds selected by an associated user interface. User preferences are then communicated to the DSP associated with earpieces 134 through wired or wireless technology, such as Wi-Fi, Bluetooth, or similar technology, for example. The wearable device 130 analyzes the current audio field and sounds 102, 104, 106, 108, 110, and 112 to determine what signals to generate to achieve the user's desired auditory scene. If the user changes preferences, the system updates the configuration to reflect the changes and apply them dynamically.

In one embodiment as generally depicted in FIG. 1, user 120 wears two in-ear or intra-aural devices 134 (one in each ear) that may be custom fitted or molded using technology similar to that used for hearing aids. Alternatively, stock sizes and/or removable tips or adapters may be used to provide a good seal and comfortable fit for different users. Devices 134 may be implemented by highly miniaturized devices that fit completely in the ear canal, and are therefore practically invisible so they do not trigger any social stigma related to hearing aid devices. This may also facilitate a more comfortable and "integrated" feel for the user. The effort and habit of wearing such devices 134 may be comparable to contact lenses where the user inserts the devices 134 in the morning, and then may forget that s/he is wearing them. Alternatively, the user may keep the devices in at night to take advantage of the system's functionalities while s/he is sleeping, as described with respect to representative use cases below.

Depending on the particular implementation, earpieces 134 may isolate the user from the ambient auditory environment through passive and/or active attenuation or cancellation, while, at the same time, reproducing only the desired sound sources either with or without enhancement or augmentation. Wearable device 130, which may be implemented within earpieces 134, may also be equipped with wireless communication (integrated Bluetooth or Wi-Fi) to connect with various external sound sources, an external user interface, or other similar wearable devices.

Figure 3:
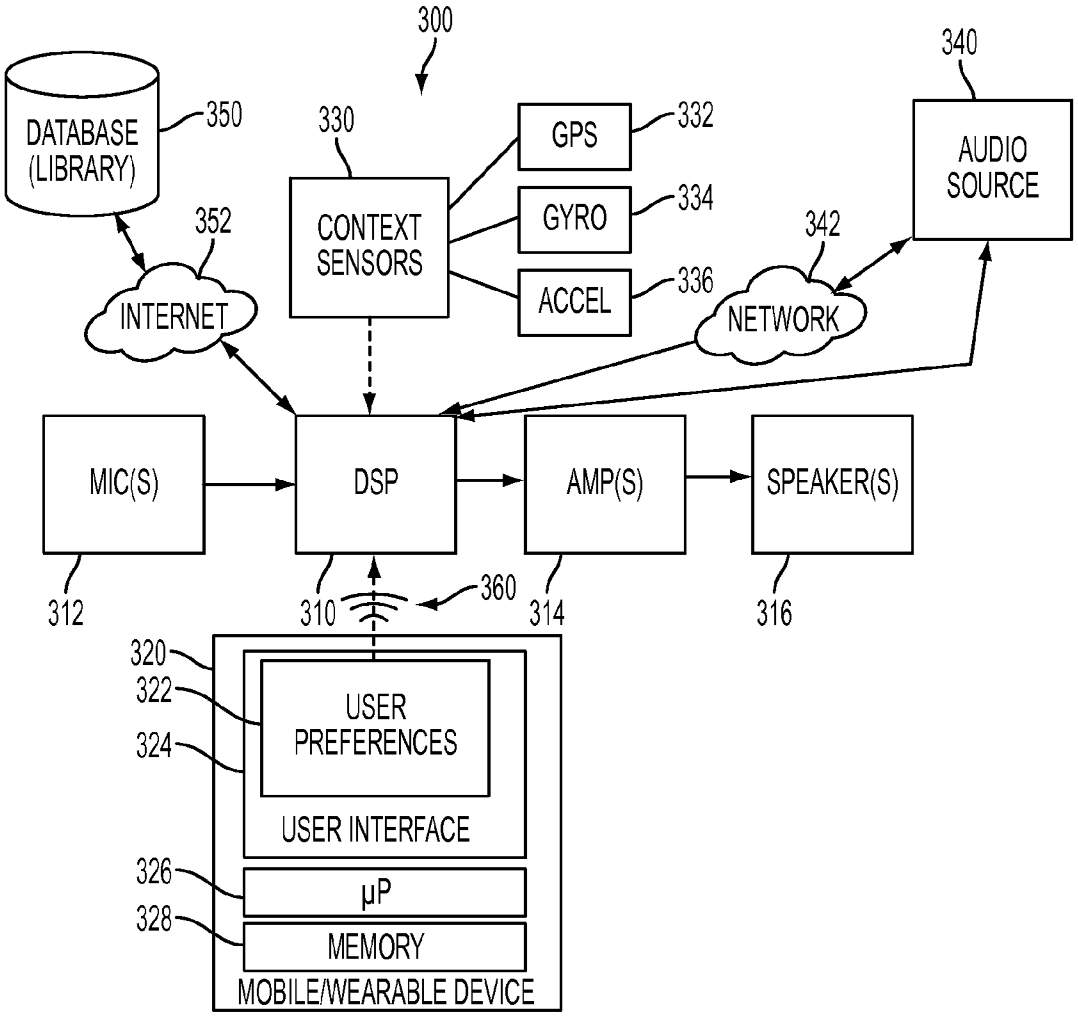
FIG. 3 is a block diagram illustrating a representative embodiment of a system for generating an auditory environment for a user based on user preferences.

Wearable device 130 may include context sensors (such as accelerometer, gyroscope, GPS, etc.; FIG. 3) to determine accurately the user's location and/or head position and orientation. This allows the system to reproduce voices and sounds in the correct spatial position as they occur within the ambient auditory environment to not confuse the user. As an example, if a voice comes from the left of the user and he turns his head 45 degrees toward his left, the voice is placed in the correct location of the stereo panorama to not confuse the user's perception. Alternatively, the system can optimize the stereo panorama of a conversation (for example, by spreading out the audio sources), which may lower the user's cognitive load in certain situations. In one embodiment, user 120 may provide user preferences to artificially or virtually relocate particular sound sources. For example, a user listening to a group conversation over a telephone or computer may position a speaker in a first location within the stereo panorama, and the audience in a second location within the stereo sound field or panorama. Similarly, multiple speakers could be virtually positioned at different locations with the auditory environment of the user as generated by wearable device 130.

Although wearable device 130 is depicted with earpieces 134, other embodiments may include various components of system 100 contained within, or implemented by, different kinds of wearable devices. For example, the speakers and/or microphones may be disposed within a hat, scarf, shirt collar, jacket, hood, etc. Similarly, the user interface may be implemented within a separate mobile or wearable device, such as a smartphone, tablet, wrist watch, arm band, etc. The separate mobile or wearable device may include an associated microprocessor and/or digital signal processor that may also be used to provide additional processing power to augment the capabilities of the main system microprocessor and/or DSP.

As also generally depicted by the block diagram of system 100 in FIG. 1, a user interface (FIGS. 5-6) allows user 120 to create a personalized or customized auditory experience by setting his/her preferences indicated by symbols 140, 142, 144, 146, for associated sound types to indicate which sounds to amplify, cancel, add or insert, or attenuate, respectively. Other functions may be used to enhance a sound by providing equalization or filtering, selective attenuation or amplification of one or more frequencies of an associated sound, or replacing an undesired sound with a more pleasant sound (using a combination of cancellation and addition/insertion, for example). The changes made by user 120 using the user interface are communicated to the wearable device 130 to control corresponding processing of input signals to create auditory output signals that implement the user preferences.

For example, the user preference setting for cancellation represented at 142 may be associated with a sound group or type of "traffic noise" 102. Wearable device 130 may provide cancellation of this sound/noise in a manner similar to noise cancelling headphones by generating a signal having a substantially similar or equal amplitude that is substantially out of phase with the traffic noise 102. Unlike conventional noise cancelling headphones, the cancellation is selective based on the corresponding user preference 142. As such, in contrast to conventional noise cancelling headphones that attempt to reduce any/all noise, wearable device 130 cancels only the sound events that the user chooses not to hear, while providing the ability to further enhance or augment other sounds from the ambient auditory environment.

Sounds within the ambient auditory environment can be enhanced as generally indicated by user preference 140. Wearable device 130 may implement this type of feature in a similar manner as performed for current hearing aid technology. However, in contrast to current hearing aid technology, sound enhancement is applied selectively in response to particular user preference settings. Wearable device 130 may actively add or insert sounds to the user's auditory field using one or more inward facing loudspeaker(s) based on a user preference as indicated at 144. This function may be implemented in a similar manner as used for headphones by playing back music or other audio streams (phone calls, recordings, spoken language digital assistant, etc.). Sound lowering or attenuation represented by user preference 146 involves lowering the volume or amplitude of an associated sound, such as people talking as represented at 108. This effect may be similar to the effect of protective (passive) ear plugs, but applied selectively to only certain sound sources in response to user preferences of user 120.

Figure 2:
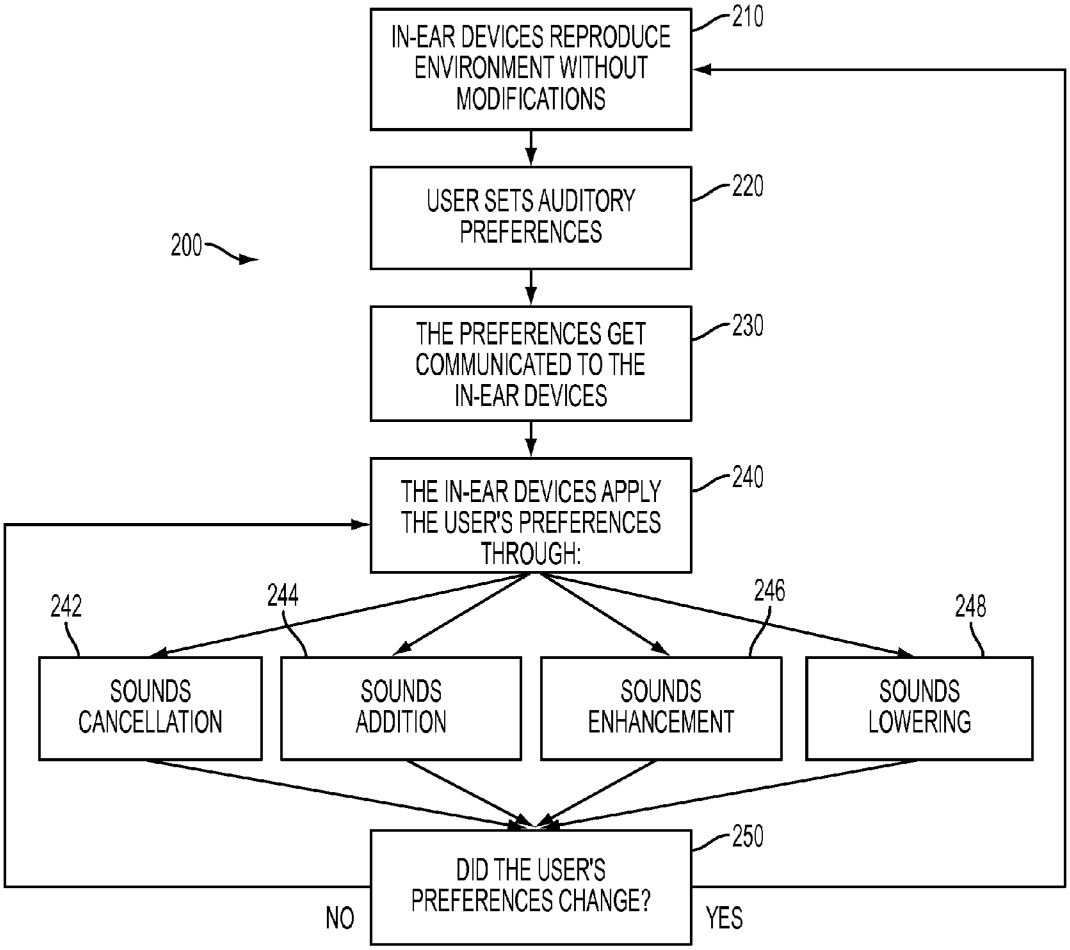
FIG. 2 is a flowchart illustrating operation of a representative embodiment of a system or method for generating a user controllable auditory environment.

FIG. 2 is a simplified flowchart illustrating operation of a representative embodiment of a system or method for generating a user controllable auditory environment. The flowchart of FIG. 2 generally represents functions or logic that may be performed by a wearable device as illustrated and described with reference to FIG. 1. The functions or logic may be performed by hardware and/or software executed by a programmed microprocessor. Functions implemented at least partially by software may be stored in a computer program product comprising a non-transitory computer readable storage medium having stored data representing code or instructions executable by a computer or processor to perform the indicated function(s). The computer-readable storage medium or media may be any of a number of known physical devices which utilize electric, magnetic, and/or optical devices to temporarily or persistently store executable instructions and associated data or information. As will be appreciated by one of ordinary skill in the art, the diagrams may represent any one or more of a number of known software programming languages and processing strategies such as event-driven, interrupt-driven, multi-tasking, multi-threading, and the like. As such, various features or functions illustrated may be performed in the sequence illustrated, in parallel, or in some cases omitted. Likewise, the order of processing is not necessarily required to achieve the features and advantages of various embodiments, but is provided for ease of illustration and description. Although not explicitly illustrated, one of ordinary skill in the art will recognize that one or more of the illustrated features or functions may be repeatedly performed.

Block 210 of FIG. 2 represents a representative default or power-on mode for one embodiment with in-ear devices reproducing the ambient auditory environment without any modifications. Depending on the particular application and implementation of the wearable device, this may include active or powered reproduction of the ambient environment to the loudspeakers of the wearable device. For example, in embodiments having intra-aural earpieces with good sealing and passive attenuation, the default mode may receive various types of sounds using one or more ambient microphones, and generate corresponding signals for one or more speakers without significant signal or sound modifications. For embodiments without significant passive attenuation, active ambient auditory environment reproduction may not be needed.

The user sets auditory preferences as represented by block 220 via a user interface that may be implemented by the wearable device or by a second microprocessor-based device such as a smartphone, tablet computer, smartwatch, etc. Representative features of a representative user interface are illustrated and described with reference to FIGS. 5 and 6. As previously described, user preferences represented by block 220 may be associated with particular types, groups, or categories of sounds and may include one or more modifications to the associated sound, such as cancellation, attenuation, amplification, replacement, or enhancement, for example.

User preferences captured by the user interface are communicated to the wearable device as represented by block 230. In some embodiments, the user interface is integrated within the user device such that communication is via a program module, message, or similar strategy. In other embodiments, a remote user interface may communicate over a local or wide area network using wired or wireless communication technology. The received user preferences are applied to associated sounds within the ambient auditory environment as represented by block 240. This may include cancellation 242 of one or more sounds, addition or insertion 244 of one or more sounds, enhancement 246 of one or more sounds, or attenuation 248 of one or more sounds. The modified sounds are then provided to one or more speakers associated with or integrated with the wearable device. Additional processing of the modified sounds may be performed to virtually locate the sound(s) within the auditory environment of the user using stereo or multiple speaker arrangements as generally understood by those of skill in the art. Modification of one or more types or categories of sounds received by one or more ambient microphones of the wearable device in response to associated user preferences continues until the user preferences change as represented by block 250.

Various embodiments represented by the flow diagram of FIG. 2 may use associated strategies to cancel or attenuate (lower volume) selected sound types or categories as represented by blocks 242 and 248, respectively.

For embodiments having intra-aural or circumaural earpieces, external sounds from the ambient auditory environment are passively attenuated before reaching the ear drums directly. These embodiments acoustically isolate the user by mechanically preventing external sound waves from reaching the ear drums. In these embodiments, the default auditory scene that the user hears without active or powered signal modification is silence or significantly reduced or muffled sounds, regardless of the actual external sounds. For the user to actually hear anything from the ambient auditory environment, the system has to detect external sounds with one or more microphones and deliver them to one or more inward-facing speakers so that they are audible to the user in the first place. Lowering or cancelling sound events may be accomplished primarily on a signal processing level. The external sound scene is analyzed, and—given the user preferences—is modified (processed) and then played back to the user through one or more inwards facing loudspeakers.

In embodiments having supra-aural earpieces or other wearable speakers and microphones including above-ear devices (e.g., traditional hearing aid), external sound is still able to reach the ear drums, so the default perceived auditory scene is mostly equivalent to the actual ambient auditory scene. In these embodiments, to lower or cancel a specific external sound event, the system has to create an active inverted sound signal to counteract the actual ambient sound signal. The cancellation signal is generated out of phase with the ambient signal sound signal so the inverted sound signal and ambient sound signal combine and cancel one another to remove (or lower toward zero) the specific sound event. Note that adding and enhancing sound events as represented by blocks 244 and 246 is done in the same way in both strategies with the sound event to be enhanced or added played back on the inward facing loudspeakers.

FIG. 3 is a block diagram illustrating a representative embodiment of a system for generating an auditory environment for a user in response to user preferences associated with one or more types or categories of ambient sounds. System 300 includes a microprocessor or digital signal processor (DSP) 310 in communication with one or more microphones 312, one or more amplifiers 314 and one or more speakers 316. System 300 may include one or more context sensors 330 in communication with DSP 310. Optional context sensors 330 may include a GPS sensor 332, a gyroscope 334, and an accelerometer 336, for example. Context sensors 330 may be used to detect a location or context of user 120 (FIG. 1) relative to a predefined or learned auditory environment, or position of the wearable device 130 (FIG. 1). In some embodiments, context sensors 330 may be used by the user interface to control the display of context-sensitive user preference controls. Alternatively, or in combination, context sensors 330 may be used by the user interface to detect user gestures to select or control user preferences as described in greater detail below with reference to representative user interfaces illustrated in FIGS. 5 and 6.

DSP 310 receives user preferences 322 captured by an associated user interface 324. In the representative embodiment illustrated in FIG. 3, user interface 324 is implemented by a second microprocessor 326 having associated memory 328 embedded in a mobile device 320, such as a smartphone, tablet computer, wrist watch, or arm band, for example. User preferences 322 may be communicated via a wired or wireless communications link 360 to DSP 310. Various types of wired or wireless communications technology or protocols may be used depending on the particular application or implementation. Representative communication technologies or protocols may include Wi-Fi or Bluetooth, for example. Alternatively, microprocessor 326 may be integrated within the same wearable device as DSP 310 rather than within a separate mobile device 320. In addition to user interface functions, mobile device 320 may provide additional processing power for system 300. For example, DSP 310 may rely on microprocessor 326 of mobile device 320 to detect the user context, to receive broadcast messages, alerts, or information, etc. In some embodiments, the system may communicate with external devices for additional processing power; e.g. a smartphone 320, a smart watch, or connect directly to remote servers using a wireless network. In these embodiments, an unprocessed audio stream may be sent to mobile device 320, which processes the audio stream and sends this modified audio stream back to DSP 310. Similarly, context sensors associated with mobile device 320 may be used to provide context information to DSP 310 as previously described.

System 300 may communicate with a local or remote database or library 350 over a local or wide area network, such as the internet 352, for example. Database or library 350 may include sound libraries having stored sounds and/or associated signal characteristics for use by DSP 310 in identifying a particular type or group of sounds from the ambient audio environment. Database 350 may also include a plurality of user preference presets corresponding to particular ambient auditory environments. For example, database 350 may represent a "Presets Store", where the user can easily download preformatted audio canceling/enhancing patterns already processed or programmed for different situations or environments. As a representative example, if the user is at a baseball game he can easily go to the Presets Store and download the pre-arranged audio enhancing pattern that will enhance the announcer's voice and the voice of the people he talks to while cancelling auditory advertisements and reducing or attenuating the crowd's noise level.

As previously described, context-sensitive sounds or data streams representing sounds may be provided from an associated audio source 340, such as a music player, an alert broadcaster, a stadium announcer, a store or theater, etc. Streaming data may be provided directly from audio source 340 to DSP 310 via a cellular connection, Bluetooth, or Wi-Fi, for example. Data streaming or downloads may also be provided over a local or wide area network 342, such as the internet, for example.

In operation, a representative embodiment of a system or method as illustrated in FIG. 3, for example, generates a customized or personalized user controllable auditory environment based on sounds from the ambient auditory environment by receiving a signal representing the sounds in the ambient auditory environment of the user from one or more microphones 312. DSP 310 processes the signal using a microprocessor to identify at least one of a plurality of types of sounds in the ambient auditory environment. DSP 310 receives user preferences 322 corresponding to each of the plurality of types of sounds and modifies the signal for each type of sound in the ambient auditory environment based on the corresponding user preference. The modified signal is output to amp(s) 314 and speaker(s) 316 to generate the auditory environment for the user. DSP 310 may receive a sound signal from an external device or source 340 in communication with DSP 310 via wired or wireless network 342. The received signal or data from the external device 340 (or database 350) is then combined with the modified types of sound by DSP 310.

As also illustrated in FIG. 3, user preferences 322 may be captured by a user interface 324 generated by a second microprocessor 326 and wirelessly transmitted to, and received by DSP 310. Microprocessor 326 may be configured for generating a context-sensitive user interface in response to the ambient auditory environment of the user, which may be communicated by DSP 310 or directly detected by mobile device 320, for example.

Figure 4:
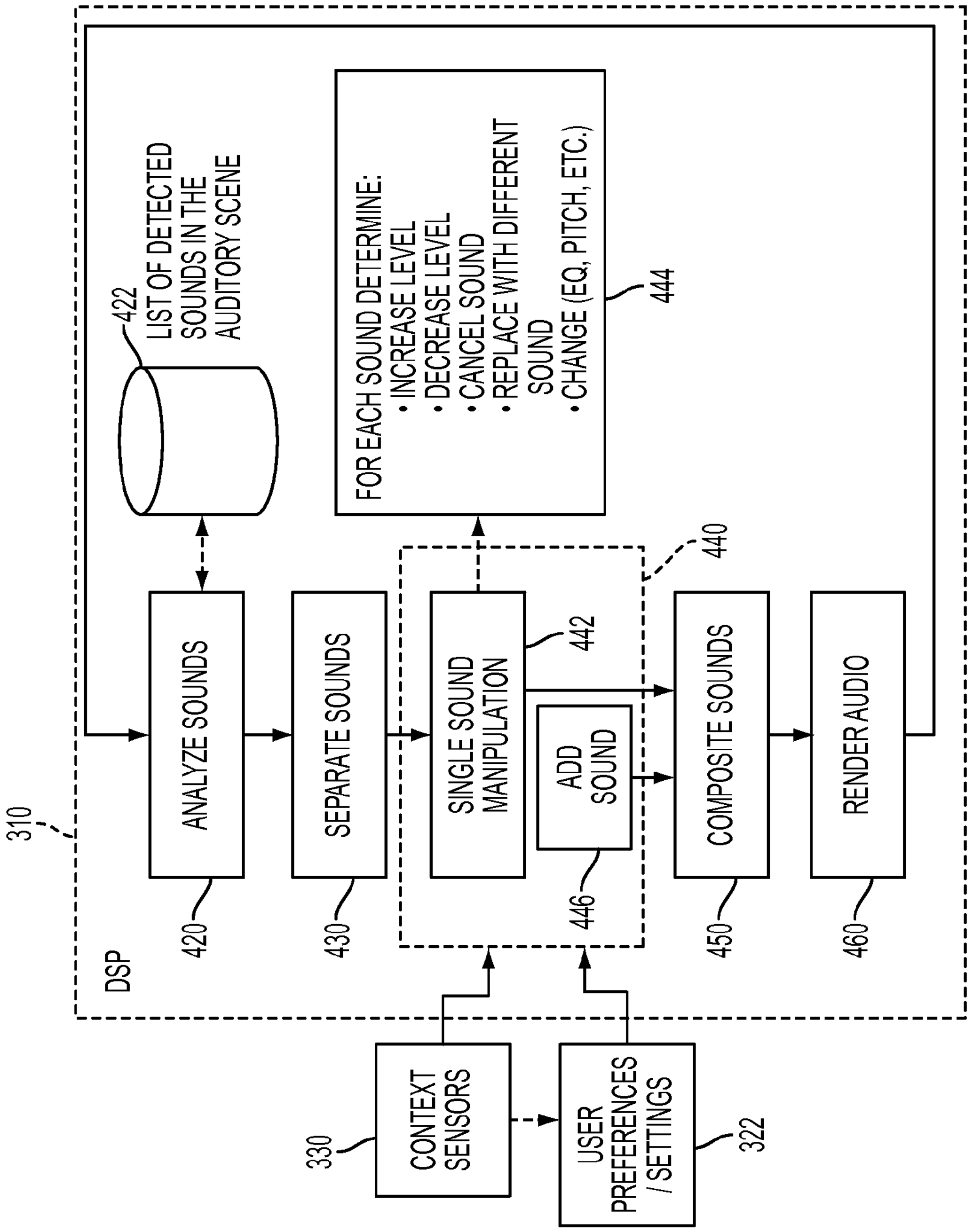
FIG. 4 is a block diagram illustrating functional blocks of a system for generating an auditory environment for a user of a representative embodiment.

FIG. 4 is a block diagram illustrating functional blocks or features of a system or method for generating an auditory environment for a user of a representative embodiment such as illustrated in FIG. 3. As previously described, DSP 310 may communicate with context sensors 330 and receive user preferences or settings 322 captured by an associated user interface. DSP 310 analyses signals representing ambient sounds as represented at 420. This may include storing a list of detected sounds identified as represented at 422. Previously identified sounds may have characteristic features or signatures stored in a database for use in identifying sounds in future contexts. DSP 310 may separate sounds or divide signals associated with particular sounds as represented at 430. Each sound type or group may be modified or manipulated as represented at 442. As previously described, this may include increasing level or volume, decreasing level or volume, canceling a particular sound, replacing a sound with a different sound (a combination of cancelling and inserting/adding a sound), or changing various qualities of a sound, such as equalization, pitch, etc., as represented by block 444. Desired sounds may be added or mixed with the sounds from the ambient auditory environment modified in response to the user preferences 322 and/or context sensors 330.

The modified sounds as manipulated by block 442 and any added sound 446 are composited or combined as represented at block 450. The audio is rendered based on the composite signal as represented at 450. This may include signal processing to generate a stereo or multi-channel audio signal for one or more speakers. In various embodiments, the combined modified signal is processed to virtually locate one or more sound sources within an auditory environment of the user based on positions of the sources within the ambient auditory environment or based on user selected spatial orientation. For example, the combined modified signal may be separated into a left signal provided to a first speaker and a right signal provided to a second speaker.

Figure 5:
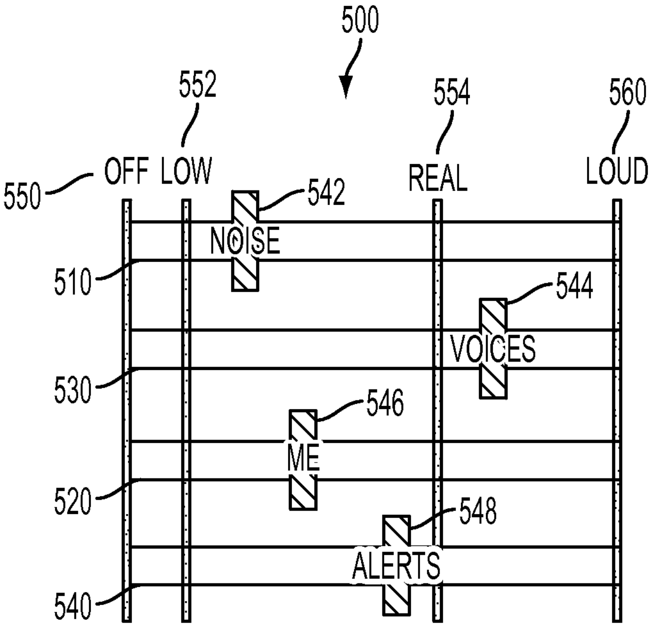
FIGS. 5 and 6 illustrate representative embodiments of a user interface having controls for specifying user preferences associated with particular types or groups of sounds.
Figure 6:
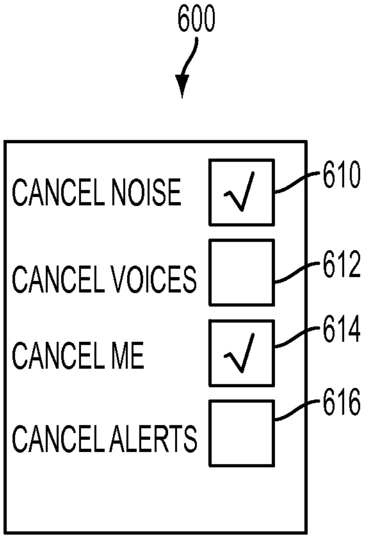

FIGS. 5 and 6 illustrate representative embodiments of a simplified user interface having controls for specifying user preferences associated with particular types or groups of sounds. The user interface allows the user to create a better auditory experience by setting preferences with respect to what sounds to hear better, not hear at all, or just dim down at the moment. The changes made by the user on this interface get communicated to the wearable device(s) for processing as previously described to amplify, attenuate, cancel, add, replace, or enhance particular sounds from the ambient auditory environment and/or external sources to create a personalized, user controlled auditory environment for the user.

The user interface may be integrated with the wearable device and/or provided by a remote device in communication with the wearable device. In some embodiments, the wearable device may include an integrated user interface for use in setting preferences when an external device is not available. A user interface on an external device may override or supplant the settings or preferences of an integrated device, or vice versa, with either the integrated user interface or remote user interface having priority depending on the particular implementation.

The user interface gives the user the ability to set auditory preferences on the fly and dynamically. Through this interface, the user can raise or lower the volume of specific sound sources as well as completely cancel or enhance other auditory events as previously described. Some embodiments include a context sensitive or context aware user interface. In these embodiments, the auditory scene defines the user interface elements or controls, which are dynamically generated and presented to the user as described in greater detail below.

The simplified user interface controls 500 illustrated in FIG. 5 are arranged with familiar slider bars 510, 520, 530, and 540 for controlling user preferences related to noise, voices, user voice, and alerts, respectively. Each slider bar includes an associated control or slider 542, 544, 546, and 548 for adjusting or mixing the relative contribution of the noise, voices, user voice, or alerts, respectively, of each type or group of sound into the auditory environment of the user. In the representative embodiment illustrated, various levels of mixing are provided ranting from "off" 550, to "low" 552, to "real" 554 to "loud" 560. When the slider is in the "off" position 550, the DSP may be attenuating the associated sound so that it cannot be heard (in the case of a direct, external sound or advertisement), or apply active cancellation to significantly attenuate or cancel the designated sound from the ambient auditory environment. The "low" position 552 corresponds to some attenuation, or relatively lower amplification of the associated sound relative to the other sounds represented by the mixer or slider interface. The "real" position 554 corresponds to substantially replicating the sound level from the ambient auditory environment to the user as if the wearable device was not being worn. The "loud" position 560 corresponds to more amplification of the sound relative to other sounds or the level of that sound in the ambient auditory environment.

In other embodiments, user preferences may be captured or specified using sliders or similar controls that specify sound levels or sound pressure levels (SPL) in various formats. For example, sliders or other controls may specify percentages of the initial loudness of a particular sound, or dBA SPL (where 0 dB is "real", or in absolute SPL). Alternatively, or in combination, sliders or other controls may be labeled "low", "normal", and "enhanced." For example, a user may move a selector or slider, such as slider 542 to a percentage value of zero (e.g., corresponding to a "Low" value) when the user would like to attempt to completely block or cancel a particular sound. Further, the user may move a selector, such as slider 544 to a percentage value of one-hundred (e.g., corresponding to a "Normal" or "Real" value) when the user would like to pass-through a particular sound. In addition, the user may move a selector, such as slider 546 to a percentage value above one-hundred (e.g., two-hundred percent) when the user would like to amplify or enhance a particular sound.

In other embodiments, the user interface may capture user preferences in terms of sound level values that may be expressed as sound pressure levels (dBA SPL) and/or attenuation/gain values (e.g., specified in decibels). For example, a user may move a selector, such as slider 548 to an attenuation value of −20 decibels (dB) (e.g., corresponding to a “Low” value) when the user would like to attenuate a particular sound. Further, the user may move a selector, such as slider 548, to a value of 0 dB (e.g., corresponding to the “Real” value 554 in FIG. 5) when the user would like to pass-through a particular sound. In addition, the user may move a selector, such as slider 548 toward a gain value of +20 dB (e.g., corresponding to the “Loud” value 560 in FIG. 5) when the user would like to enhance a particular sound by increasing the loudness of the sound.

In the same or other embodiments, a user may specify the sound pressure level at which a particular sound is to be produced for the user. For example, the user may specify that an alarm clock sound is to be produced at 80 dBA SPL, while a partner’s alarm clock is to be produced at 30 dBA SPL. In response, the DSP 310 (FIG. 3) may increase the loudness of the user’s alarm (e.g., from 60 dBA SPL to 80 dBA SPL) and reduce the loudness of the user’s alarm (e.g., from 60 dBA SPL to 30 dBA SPL).

The sliders or similar controls can be relatively generic or directed to a broad group of sounds such as illustrated in FIG. 5. Alternatively, or in combination, sliders or other controls may be directed to more specific types or classes of sounds. For example, individual preferences or controls may be provided for “Voices of the people you are having a conversation with” vs. “Other Voices” or “TV voices” vs. “My partner’s voice”. Similarly, controls for alerts may include more granularity for specific types of alerts, such as car alerts, phone alerts, sirens, PA announcements, advertisements, etc. A general control or preference for Noises may include sub-controls or categories for “birds”, “traffic”, “machinery”, “airplane”, etc. The level of granularity is not limited by the representative examples illustrated and may include a virtually unlimited number of types of pre-defined, learned, or custom created sounds, sound groups, classes, categories, types, etc.

FIG. 6 illustrates another simplified control for a user interface used with a wearable device according to various embodiments of the present disclosure. Control 600 includes check boxes or radio buttons that can be selected or cleared to capture user preferences with respect to particular sound types or sources. The representative control listed includes check boxes to cancel noise 610, cancel voices 612, cancel the user voice (“me”) 614, or cancel alerts 616. The check boxes or similar controls may be used in combination with the sliders or mixers of FIG. 5 to provide a convenient method for muting or canceling particular sounds from the auditory environment of the user.

As previous described, various elements of the user interface, such as the representative controls illustrated in FIGS. 5 and 6 may be always present/displayed, i.e. the most common sounds are already present, the displayed controls may be context-aware based on a user location or identification of particular sounds within the ambient auditory environment, or a combination of the two, i.e. some controls always present and others context-aware. For example, a general “Noise” control may always be displayed with an additional slider “Traffic Noise” being presented on the user interface when traffic is present or when the user interface detects the user being in a car or near a freeway. As another example, one auditory scene (user walking on the sidewalk) may include traffic sounds, so a slider with the label “traffic” is added. If the scene changes, e.g., the user is at home in the living room where there is no traffic noise, the slider labeled “traffic” disappears. Alternatively, the user interface could be static and contain a large amount of sliders that are labeled with generic terms, such as “voices”, “music”, “animal sounds”, etc. The user may also be provided the capability to manually add or remove particular controls.

While graphical user interface controls are illustrated in the representative embodiments of FIGS. 5 and 6, other types of user interfaces may be used to capture user preferences with respect to customizing the auditory environment of the user. For example, voice activated controls may be used with voice recognition of particular commands, such as “Lower Voices” or “Voices Off”. In some embodiments, the wearable device or linked mobile device may include a touch pad or screen to capture user gestures. For example, the user draws a character “V” (for voices), then swipes down (lowering this sound category). Commands or preferences may also be captured using the previously described context sensors to identify associated user gestures. For example, the user flicks his head to left (to selects voices or sound type coming from that direction), the wearable device system speaks to request confirmation “voices?”, then the user lowers head (meaning, lowering this sound category). Multi-modal input combinations may also be captured: e.g., user says “voices!” and at the same time swipes down on ear cup touch pad to lower voices. The user could point to a specific person and make a raise or lower gesture to amplify or lower the volume of that person’s voice. Pointing to a specific device may be used to specify the user wants to change the volume of the alarm for that device only.

In some embodiments, different gestures are used to specify a “single individual” and a “category” or type of sound. If the users points to a car with the first gesture, the system changes levels to the sounds emitted by that specific vehicle. If the user points to a car with the second kind of gesture (e.g. 2 fingers pointing instead of one, open hand pointing, or other) the system interprets the volume changes as referring to the whole traffic noise (all cars and similar).

The user interface may include a learning mode or adaptive function. The user interface may adapt to user preferences using any one of a number of heuristic techniques or machine learning strategies. For example, one embodiment includes a user interface that learns what sounds are “important” to a specific user based on user preference settings. This may be done using machine learning techniques that monitor and adapt to the user over time. As more and more audio data is collected by the system, the system is better able to prioritize the sounds based upon user preference data, user behavior, and/or a general machine learning model that helps classify what sounds are valuable on a general basis and/or a per user basis. This helps the system to be intelligent about how to mix the various individual sounds automatically as well.

Illustrative Examples of Use/Operation of Various Embodiments

Use Case 1:

The user is walking down a trafficked downtown road and does not want to hear any car noise, but still wants to hear other people’s voices, conversations, and sounds of nature. The system filters out the traffic noise while, at the same time, enhancing people’s voices and sounds of nature. As another example, selective noise cancellation can be applied to a phone call to allow only certain sounds to be heard, others to be enhanced, and others to just be lowered. The user may be talking to someone on the phone who is calling from a noisy area (airport). The user cannot easily hear the speaker because of background noise, therefore the user adjusts preferences using the user interface, which presents multiple sliders to control the different sounds being received from the phone. The user can then lower the slider relative to "background voices/noises" and/or enhance the speaker's voice. Alternatively (or in addition) the speaker may also having a user interface and is courteous enough to lower the background noise level on his side during the phone call. This type of use is even more relevant with multi-party calls where background noise accumulates from each caller.

Use Case 2:

The user is about to go for a run. She sets the wearable device preferences using a user interface on her smartphone. She decides to keep hearing the traffic noise to avoid being hit by a vehicle, however she chooses to dim it down. She selects a playlist to be streamed in her ears at a certain volume from her smartphone or another external device and she chooses to enhance the sound of birds and nature to make this run even more enjoyable.

Use Case 3:

The user is in the office and he is busy finishing up a time sensitive report. He sets the system to "Focus mode," and the system blocks any office noises as well as the people voices and conversations happening around him. At the same time, the headphones are actively listening for the user's name, and will let a conversation pass through if it is explicitly addressed to the user (which is related to the cocktail party effect).

Use Case 4:

The user is at a baseball game and he wants to enhance his experience by performing the following auditory adjustments: lower the crowd's cheering noise; enhance the commenter and presenter's voice; hear what the players in the field are saying; and still being able to talk to the person next to him or order hot dogs and hear those conversations perfectly fine (thanks to audio level enhancement).

Use Case 5:

The user chooses to "beautify" certain sounds (including his own voice). He chooses to make the colleagues' voices more pleasant and to change the sound of typing on computer keyboards to the sound of raindrops on a lake.

Use Case 6:

The user wants to hear everything except for the voice of a specific colleague who usually bothers him. His perception of sounds and conversations is not altered in any way except for the voice of that specific person, which is cancelled out.

Use Case 7:

The user chooses to hear his own voice differently. Today he wants to hear himself talk with the voice of James Brown. Alternatively, the user can choose to hear his own voice with a foreign accent. This voice is played back on the inward-facing speakers, so that only the user himself hears the voice.

Use Case 8:

The user receives a call on his phone. The communication is streamed directly to his in-ear devices in a way that still allows him to hear the environment and the sounds around him, but at the same time can hear the person on the phone loud and clear. The same could be done when the user is watching TV or listening to music. He can have those audio sources streaming directly to his in-ear pieces.

Use Case 9:

The user listens to music on his in-ear devices, streamed directly from his mobile device. The system plays back the music in a very spatial way that allows him to hear the sounds of his surroundings. The effect is similar to listening to music playing from a loud speaker placed next to the user. It's not obstructing other sounds, but at the same time hearable only by the user.

Use Case 10:

The user is having a conversation with a person who speaks a foreign language. The in-ear pieces provide him a real-time in-ear language translation. The user hears the other person speak English in real time even if the other person is speaking a different language.

Use Case 11:

The user can receive location based in-ear advertisement ("Turn left for 50% off at the nearby coffee house")

Use Case 12:

The user is in a conference. The speaker on the podium is talking about a less interesting topic (at least, not interesting for the user) and an important email arrives. In order to isolate himself, the user could put on his noise control headphones but that would be very un-polite toward the speaker. Instead the user can just set his in-ear system to "complete noise cancellation", acoustically isolating himself from the environment, and giving him the quiet environment he needs to focus.

Use Case 13:

In a domestic life scenario where partners sleep in proximity and one of the two snores, the other user could selectively cancel the snoring noise without at the same time canceling any other sound from the environment. This would allow the user to still be able to hear the alarm clock in the morning or other noises (such as a baby crying in the other room) that would not be possible to hear with traditional ear plugs. The user can also set his system to cancel his partner's alarm clock noise but still be able to hear his own alarm clock.

Use Case 14:

The user is in an environment where there is constant background music, e.g., from a PA system in a store, or from a colleague's computer in an office. The user sets his preferences then to "kill all ambient music" around him, without modifying any other sound of the sound scene.

As demonstrated by various embodiments of the present disclosure described above, the disclosed systems and methods create a better auditory user experience and may improve the user's hearing capabilities through augmentation and/or cancellation of sounds and auditory events. Various embodiments facilitate an augmented reality audio experience where specific sounds and noises from the environment can be cancelled, enhanced, replaced, or other sounds inserted or added with extreme ease of use. A wearable device or related method for customizing a user auditory environment may improve hearing capabilities, attention, and/or concentration abilities of a user by selectively processing different types or groups of sounds based on different user preferences for various types of sounds. This may result in lower cognitive load for auditory tasks and provide stronger focus when listening to conversations, music, talks, or any kind of sounds. Systems and methods for controlling a user auditory environment as previously described may allow the user to enjoy only the sounds that he/she desires to hear from the auditory environment, enhance his/her auditory experience with functionalities like beautification of sounds and real-time translations during conversations, stream audio and phone conversations directly to his/her ears and be freed from the need of holding a device next to his/her ear, and add any additional sounds (e.g. music, voice recordings, advertisements, informational messages) to his/her auditory field, for example.

While the best mode has been described in detail, those familiar with the art will recognize various alternative designs and embodiments within the scope of the following claims. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments discussed herein that are described as less desirable than other embodiments or prior art implementations with respect to one or more characteristics are not outside the scope of the disclosure and may be desirable for particular applications.

What is claimed is:

1. A method for generating an auditory environment for a user, the method comprising:

receiving a signal representing an ambient auditory environment of the user;

processing the signal using a microprocessor to identify at least one type of sound included in a plurality of types of sounds in the ambient auditory environment;

in response to identifying the at least one type of sound, generating, via the microprocessor, a context-sensitive user interface corresponding to the at least one type of sound in the ambient auditory environment;

receiving, via the context-sensitive user interface, user preferences corresponding to each of the plurality of types of sounds;

modifying the signal for each type of sound in the ambient auditory environment based on the corresponding user preference; and outputting the modified signal to at least one speaker to generate the auditory environment for the user.

2. The method of claim 1 further comprising:

receiving a sound signal from an external device in communication with the microprocessor; and combining the sound signal from the external device with the modified types of sound.

3. The method of claim 2 wherein receiving a sound signal from an external device comprises wirelessly receiving a sound signal.

4. The method of claim 2 wherein receiving a sound signal comprises receiving a sound signal from a database having stored sound signals of different types of sounds.

5. The method of claim 1 wherein receiving user preferences comprises wirelessly receiving the user preferences from a user interface generated by a second microprocessor.

6. The method of claim 1 wherein generating the context-sensitive user interface comprises displaying a plurality of controls corresponding to the plurality of types of sounds in the ambient auditory environment.

7. The method of claim 1 further comprising:

dividing the signal into a plurality of component signals each representing one of the plurality of types of sounds;

modifying each of the component signals for each type of sound in the ambient auditory environment based on the corresponding user preference;

generating a left signal and a right signal for each of the plurality of component signals based on a corresponding desired spatial position for the type of sound within the auditory environment of the user;

combining the left signals into a combined left signal; and combining the right signals into a combined right signal.

8. The method of claim 7 wherein outputting the modified signal comprises outputting the combined left signal to a first speaker and outputting the combined right signal to a second speaker.

9. The method of claim 1 wherein modifying the signal for each type of sound comprises at least one of attenuating the signal, amplifying the signal, and equalizing the signal.

10. The method of claim 1 wherein modifying the signal comprises replacing one type of sound with another type of sound.

11. The method of claim 1 wherein modifying the signal comprises cancelling at least one type of sound by generating an inverse signal having substantially equal amplitude and substantially opposite phase relative to the one type of sound.

12. The method of claim 1 further comprising:

generating a user interface configured to capture the user preferences using a second microprocessor embedded in a mobile device; and wirelessly transmitting the user preferences captured by the user interface from the mobile device.

13. The method of claim 12 wherein the user interface captures user gestures to specify at least one user preference associated with one of the plurality of types of sounds.

14. A system for generating an auditory environment for a user, the system comprising:

a speaker;

a microphone; and a processor coupled to the speaker and the microphone and configured to:

receive an ambient audio signal from the microphone representing an ambient auditory environment of the user, process the ambient audio signal to identify at least one type of sound included in a plurality of types of sounds in the ambient auditory environment, in response to identifying the at least one type of sound, generate a context-sensitive user interface corresponding to the at least one type of sound in the ambient auditory environment, modify the at least one type of sound based on user preferences received via the context-sensitive user interface, and output the modified sound to the speaker to generate the auditory environment for the user.

15. The system of claim 14 wherein the context-sensitive user interface comprises a touch-sensitive surface in communication with a microprocessor configured to associate user touches with the plurality of controls.

16. The system of claim 15 wherein the context-sensitive user interface comprises a mobile phone programmed to display the plurality of controls, generate signals in response to the user touches relative to the plurality of controls, and to communicate the signals to the processor.

17. The system of claim 14 wherein the speaker and the microphone are disposed within an ear bud configured for positioning within an ear of the user.

18. The system of claim 14 wherein the context-sensitive user interface comprises a plurality of controls corresponding to the plurality of types of sounds in the ambient auditory environment.

19. The system of claim 14 wherein the processor is configured to modify the at least one type of sound by attenuating, amplifying, or cancelling the at least one type of sound.

20. The system of claim 14 wherein the processor is configured to compare the ambient audio signal to a plurality of sound signals to identify the at least one type of sound in the ambient auditory environment.

21. A non-transitory computer readable storage medium storing program code that, when executed by a microprocessor, configures the microprocessor to generate an auditory environment by performing the steps of:

processing an ambient audio signal to separate the ambient audio signal into component signals;

identifying at least one type of sound in the ambient audio signal based on at least one of the component signals;

in response to identifying the at least one type of sound, generating a context-sensitive user interface in response to identifying the at least one type of sound in the ambient audio signal;

modifying the component signals in response to corresponding user preferences received via the context-sensitive user interface; and combining the modified component signals to generate an output signal.

22. The non-transitory computer readable storage medium of claim 21 wherein the program code further configures the microprocessor to change at least one of an amplitude or a frequency spectrum of the component signals in response to the user preferences.

23. The non-transitory computer readable storage medium of claim 21, wherein the context-sensitive user interface comprises a plurality of controls, each control corresponding to a different type of sound included in the plurality of types of sounds.

24. The non-transitory computer readable storage medium of claim 23, wherein the program code further configures the microprocessor to perform the steps of:

identifying a second plurality of types of sounds included in a second ambient audio signal; and in response to identifying a second plurality of types of sounds, generating a second context-sensitive user interface, wherein the second context-sensitive user interface comprises a second plurality of controls corresponding to the second plurality of types of sounds, and the second context-sensitive user interface includes at least one control that is included in the context-sensitive user interface and at least one control that is not included in the context-sensitive user interface.

25. The non-transitory computer readable storage medium of claim 21, wherein the at least one type of sound comprises two or more types of sounds, and the context-sensitive user interface corresponding to the two or more types of sounds is generated by the microprocessor in response to identifying the two or more types of sounds in the ambient audio signal.

26. The non-transitory computer readable storage medium of claim 21, wherein the program code further configures the microprocessor to perform the steps of:

identifying a second type of sound included in a second ambient audio signal; and in response to identifying a second type of sound, automatically generating a second context-sensitive user interface, wherein the second context-sensitive user interface comprises a second plurality of controls corresponding to the second type of sound, and the second context-sensitive user interface includes at least one control that is included in the context-sensitive user interface and at least one control that is not included in the context-sensitive user interface.

* * * * *